United States Patent [19]

Caumont

[11] 4,344,426
[45] Aug. 17, 1982

[54] STERILIZABLE SURGICAL PAD

[75] Inventor: Jean-Francois Caumont, Brionne, France

[73] Assignee: Tempo Sanys, Paris, France

[21] Appl. No.: 164,462

[22] Filed: Jun. 30, 1980

[30] Foreign Application Priority Data

Dec. 10, 1979 [FR] France ................................ 79 30253

[51] Int. Cl.³ ............................................. A61L 15/00
[52] U.S. Cl. .................................... 128/156; 128/287; 128/296
[58] Field of Search ................... 128/287, 290 R, 296, 128/156

[56] References Cited

U.S. PATENT DOCUMENTS

| 2,649,859 | 8/1953 | Hermanson et al. | 128/287 |
| 2,896,626 | 7/1959 | Voigtman | 128/287 |
| 3,067,747 | 12/1962 | Wolterding et al. | 128/296 |
| 3,683,917 | 8/1972 | Comerford | 128/290 R |
| 3,913,580 | 10/1975 | Ginocchio | 128/290 W |
| 4,079,739 | 3/1978 | Whitehead | 128/296 |

Primary Examiner—C. Fred Rosenbaum
Attorney, Agent, or Firm—Seidel, Gonda, Goldhammer & Panitch

[57] ABSTRACT

This invention concerns a sterilizable surgical pad comprising a flat core made from an absorbent material, e.g. absorbent cotton wool, held in shape by means of a sheet of a natural or artificial textile material, such as gauze or non-woven, which surrounds the inner and side surfaces of the core and is folded over its outer surface.

7 Claims, 2 Drawing Figures

U.S. Patent      Aug. 17, 1982      4,344,426
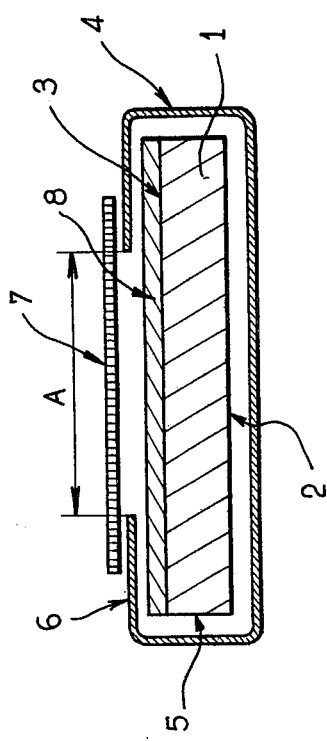
FIG_1
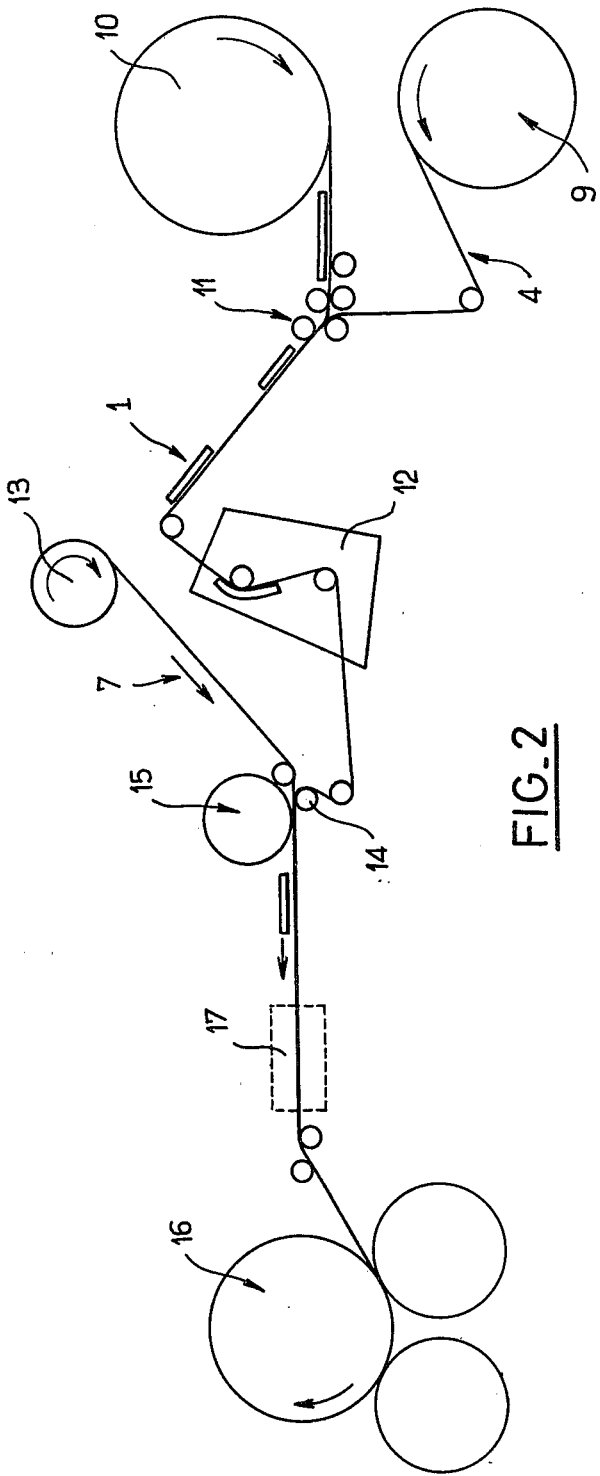
FIG_2

STERILIZABLE SURGICAL PAD

This invention relates to a sterilizable surgical pad, and apparatus for the continuous manufacture of such a pad.

There are at the present time various types of surgical pads intended particularly for covering wounds, more particularly post-operative wounds.

Pads of this kind are required to comprise an absorbent part adapted to come into contact with the wound, and a water-repellent part adapted to prevent any flow of blood or other liquids through the dressing.

Of course the first characteristic required of a surgical pad is that it should be sterilizable by the three conventional processes, i.e. irradiation (gamma or cobalt bomb radiation), treatment with ethylene oxide and, more particularly, treatment with steam in an autoclave at a temperature of about 140° C. for approximately 40 minutes.

The conventional pads adapted to satisfy these various criteria generally consist of an absorbent material, e.g. absorbent cotton wool, the outer surface of which is not intended to come into contact with the wound. The absorbent material is covered by a layer of water-repellent material, such as raw cotton, the whole being surrounded by a sheet of a natural or artifical textile material such as gauze or a non-woven. These various parts are held in position by sewing or sticking together the two edges of the textile sheet, which must overlap for that reason.

Although pads of this kind are satisfactory hygienically, they are extremely expensive, on the one hand because of the high cost of gauze, which has to be used in excess because of the essential overlapping of the edges folded over the outer surface of the pad and, on the other hand, because of the sticking or sewing operation.

The object of this invention is to obviate these disadvantages by proposing a pad of the above type, the cost of manufacture of which is very much less than that of pads used heretofore, but which at the same time offers every guarantee hygienically.

To this end, the invention relates to a sterilizable surgical pad comprising a flat core made from an absorbent material, e.g. absorbent cotton wool, held in shape by means of a sheet of a natural or artificial textile material, such as gauze or non-woven, which surrounds the inner and side surfaces of the core and is folded over its outer surface, the pad being characterized in that the textile sheet is held on the core by means of a sealing-tight film stuck by thermal welding to the outer surface of the core surrounded by the textile sheet.

This arrangement greatly improved the cost of surgical pads since, on the one hand, it does away with the sewing or sticking operations, since it is no longer necessary for the edges of the sheet of gauze to overlap on the outer part of the pad in order to enable sewing or sticking to be carried out there.

To reduce the cost of the pads still further, and according to another feature of the invention, the textile sheet does not cover all of the outer surface of the core, and this greatly reduces the amount of gauze required for the manufacture of a pad.

Further savings can be obtained by doing away with the water-repellent part of the pad, e.g. of raw cotton, since the film provides the necessary barrier on the outside of the pad.

Of course, the sealing-tight film may be arbitrarily selected provided that it has acceptable sealing properties and satisfies the above criteria as regards sterilizability.

For example, a plastic film coated on its inner surface with an adhesive adapted to be connected to the cotton wool by thermal welding may be used.

According to a preferred characteristic of the invention, the sealing-tight film comprises a co-extruded film consisting of a plurality of thicknesses of different materials extruded simultaneously.

In that case, the outer surface of the film comprises a thermoplastic material such as a polyamide or a polyester adapted to withstand a temperature of 140° C. for at least 40 minutes, and its inner surface comprises another high melt index thermoplastic, i.e. a thermoplastic which melts at a lower temperature than the polyamide or polyester making up the rest of the film and which adheres, at that temperature, to the cotton wool or gauze of the pad. The inner surface is adapted to be stuck to the absorbent material, more particularly cotton wool, by hot pressing.

The invention also relates to apparatus for the continuous manufacture of a surgical pad as described above.

Apparatus of this kind is characterised in that it comprises a reel of textile sheet, more particularly gauze, a reel for absorbent material, more particularly cotton wool, which co-operates with cutting means where applicable, means adapted to fold the gauze over the core, a reel of sealing film, a heating cylinder adapted to exert sufficient pressure on the pad to stick the sealing-tight film to its outer part, and means for packing the pads.

This system greatly reduces the manufacturing costs of the pad, since the heating cylinder system is clearly less complex than the sewing machine conventionally used, particularly in light of the fact that it saves a considerable proportion of expensive gauze.

The surgical pad and the apparatus for its production according to the invention are described in greater detail with reference to the accompanying drawings wherein:

FIG. 1 is a section of a pad of this kind.

FIG. 2 is a diagram showing an installation used for the manufacture of this pad in the form of a continuous string.

Referring to FIG. 1, the pad according to the invention consists of a flat core 1 of absorbent material, such as absorbent cotton wool, the inner part 2 of which is intended to come into contact with the wound, while its outer part 3 is in communication with the atmosphere.

The core 1 is surrounded by a sheet 4 of a natural or artificial textile material, e.g. gauze or a non-woven, which surrounds its inner surface 2 and side surfaces 5, the edges 6 being folded over the outer surface 3.

The system comprising the core 1 and the sheet 4 is held in shape by means of a sealing-tight film 7, which is thermally welded to the top surface 3 of the core 1 surrounded by the edges 6 of the textile sheet 4.

The edges 6 simply have to overlap at the film 7 to ensure security. This arrangement eliminates the need for a considerable quantity of the sheet 4, e.g. of gauze, which is an extremely expensive product.

The film 7 must on the one hand have an outer surface offering satisfactory sealing properties with respect to water and impurities in the ambient air, and on the other hand, have an inner surface enabling it to be secured to the cotton wool by thermal welding. The finished pad must also be able to withstand the various sterilization operations, more particularly at a temperature of 140° C. for at least 40 minutes.

For this purpose, the film 7 may be a (flexible) plastic film, the inner surface of which is coated with any adhesive.

Particularly satisfactory results are obtained by the use of a co-extruded film 7 of several thicknesses of different materials extruded simultaneously.

In that case, the outer surface of the film 7 is a thermoplastic, e.g. a polyamide or polyester adapted to withstand a temperature of 140° C. for at least 40 minutes, and its inner surface consists of another high melt index thermoplastic adapted to be fixed on the core 1, more particularly of cotton-wool, by hot pressing.

In that case it should be noted that if the operation for sticking the inner part of the film 7 on the cotton wool 1 is carried out at a temperature below 140° C., this does not give rise to any appreciable drawbacks, since during the sterilization operation the pads are held on one another and are not likely to undergo deformation due to softening of the thermoplastic forming the inner layer of the film 7.

If a co-extruded film 7 is used, sufficient sealing properties are obtained to be able to dispense with the waterproof part 8.

Referring to FIG. 2, the apparatus according to the invention for the continuous manufacture of the pad shown in FIG. 1 comprises a reel 9 for dispensing a web of textile sheeting 4, e.g. gauze. This reel 9 co-operates with a reel 10 consisting of a web of material forming the core, e.g. cotton wool. In the case of a string of pads, the reel 10 may rotate with a stepwise motion, and co-operates with cutting means 11 to dispense at predetermined times above the web of gauze 4, which moves continuously as far as folding means 12 at the outlet of which the gauze sheet 4 is folded over the outer surface 3 of the cores 1.

The installation further comprises a means 13 for dispensing film 7 prepared during a previous operation. Film 7 is dispensed in a means 14 above each of the cores 1 surrounded by film 4 and the combination then passes over or beneath a heated cylinder 15 adapted to apply a flexible pressure to the film 7 to allow it to be fixed on the cotton wool by thermal welding.

The combination is then fed to a suitable packing system 16.

The apparatus according to the invention is clearly advantageous over the prior-art apparatus, since the addition of the sheet 7 does away with the need for an appreciable quantity of gauze represented by arrow A in FIG. 1, thus greatly reducing the cost price of the surgical pad and, in addition, this apparatus does away with the need for a sewing machine or a gluing device, e.g. hot-melt nozzles as shown in broken lines at 17 in FIG. 2, again greatly reducing the cost price of the apparatus.

I claim:

1. A sterilizable surgical pad comprising:
    a flat core made from an absorbent material held in shape by means of a sheet of a natural or artificial textile material;
    said textile sheet surrounding the inner and side surfaces of the core and folded over the edges of the outer surface of said core;
    said textile sheet being held around the core by means of an impermeable co-extruded thermoplastic film adhered to both the outer surface of the core and the outer surface of the edges of the textile sheet which have been folded over the outer surface of the core;
    said film being able to withstand temperatures necessary to effect heat-sterilization.

2. A surgical pad in accordance with claim 1 wherein the absorbent material is cotton wool.

3. A surgical pad in accordance with claim 1 wherein the textile material is guaze or non-woven.

4. A surgical pad in accordance with claim 1 wherein the textile sheet does not cover the entire outer surface of the core.

5. A surgical pad in accordance with claim 1 or 4 wherein the impermeable thermoplastic film is a plastic film coated with an adhesive on the inner surface.

6. A surgical pad in accordance with claim 1 or 4 wherein the impermeable thermoplastic film is adhered by thermal welding.

7. A surgical pad film in accordance with claims 1 or 4 wherein the outer surface of said film is polyamide or polyester, adapted to withstand a temperature of 140° C. for at least forty minutes, and the inner surface of said film is another high melt-index thermoplastic adapted to be adhered to the core by hot pressing.

* * * * *